US006864489B2

(12) United States Patent
Chen et al.

(10) Patent No.: US 6,864,489 B2
(45) Date of Patent: Mar. 8, 2005

(54) METHOD OF DETECTING WEAR ON A SUBSTRATE USING A FLUORESCENT INDICATOR

(75) Inventors: Yen Lane Chen, New Brighton, MN (US); Gary S. Williamson, Hudson, WI (US)

(73) Assignee: 3M Innovative Properties Company, Saint Paul, MN (US)

(*) Notice: Subject to any disclaimer, the term of this patent is extended or adjusted under 35 U.S.C. 154(b) by 182 days.

(21) Appl. No.: 10/003,217

(22) Filed: Oct. 30, 2001

(65) Prior Publication Data

US 2003/0081203 A1 May 1, 2003

(51) Int. Cl.⁷ .......................... G01J 3/00; G01N 21/00
(52) U.S. Cl. .................. 250/461.1; 356/317; 356/417
(58) Field of Search ..................... 356/300, 317–318; 250/458.1–461.2, 302

(56) References Cited

U.S. PATENT DOCUMENTS

| | | | | |
|---|---|---|---|---|
| 4,327,155 A | * | 4/1982 | Hanneman | 356/318 |
| 4,444,701 A | * | 4/1984 | Meguiar | 264/40.1 |
| 4,802,762 A | * | 2/1989 | Hill, Jr. | 356/318 |
| 4,858,465 A | | 8/1989 | Molina | 73/104 |
| 4,923,726 A | * | 5/1990 | Maruyama et al. | 428/41.6 |
| 5,023,019 A | * | 6/1991 | Bumpus | 252/607 |
| 5,110,684 A | | 5/1992 | Cooper | |
| 5,144,773 A | * | 9/1992 | Flores et al. | 451/8 |
| 5,310,604 A | | 5/1994 | Melancon et al. | |
| 5,412,219 A | | 5/1995 | Chappelle et al. | 250/461 |
| 5,516,591 A | * | 5/1996 | Feldstein | 428/548 |
| 5,606,171 A | | 2/1997 | Neckers et al. | |
| 5,663,016 A | * | 9/1997 | Hong | 430/5 |
| 6,160,149 A | | 12/2000 | Dauth et al. | 556/420 |
| 6,207,720 B1 | | 3/2001 | Maeda et al. | |
| 6,391,226 B1 | * | 5/2002 | Chauvette et al. | 252/399 |
| 2003/0012599 A1 | * | 1/2003 | Wallgren et al. | 404/14 |

FOREIGN PATENT DOCUMENTS

| | | | | |
|---|---|---|---|---|
| CA | 2137298 | 4/1996 | | G01N/21/91 |
| EP | 0 776 873 | 6/1997 | | |

* cited by examiner

Primary Examiner—F. L. Evans
Assistant Examiner—Kara Geisel
(74) Attorney, Agent, or Firm—Sean J. Edman

(57) ABSTRACT

A method of detecting wear on a substrate including coating a composition that includes a fluorescent compound on the surface of a first substrate, exposing the coated surface to wear, exposing the coated surface to radiation capable of exciting the fluorescent compound, and detecting the presence or absence of fluorescence.

33 Claims, 2 Drawing Sheets

METHOD OF DETECTING WEAR ON A SUBSTRATE USING A FLUORESCENT INDICATOR

BACKGROUND OF THE INVENTION

The invention relates to detecting wear on a coated substrate.

Coatings and finishes are often applied to floors, walls and counter tops to improve durability, alter aesthetics, decrease maintenance requirements, prevent microorganism growth, and impart water resistance and chemical resistance to the surface. The coatings and finishes are often applied in several coating applications to obtain a finish having the desired appearance and durability. Because these coatings and finishes are often clear and colorless, it can be difficult to determine whether the surface coverage is complete.

As the surface is used, for example, contact with pedestrian traffic in the case of floors, the coating begins to wear to a point at which the coating is no longer providing its intended function. It is often difficult to determine the point at which the coating becomes worn to such an extent that the surface should be refinished. It would be helpful to be able to easily determine when a surface coating has worn to at point at which the surface is in need of refinishing.

SUMMARY

In one aspect, the invention features a method of detecting wear on a substrate. The method includes coating a composition that includes a fluorescent compound on the surface of a substrate, exposing the coated surface to wear, exposing the coated surface to radiation capable of exciting the fluorescent compound, and detecting the presence or absence of fluorescence.

In one aspect, the invention features a method of detecting wear on a substrate, the method including coating a composition that includes a fluorescent compound on the surface of a substrate, exposing the coated surface to wear, exposing the coated surface to radiation capable of exciting the fluorescent compound, and detecting the presence or absence of fluorescence. In one embodiment, the radiation includes ultraviolet light. In other embodiments, the radiation has a wavelength of from 200 nm to 400 nm. In one embodiment, the fluorescent compound emits visible light. In other embodiments, the fluorescent compound emits radiation having a wavelength of from 400 nm to 750 nm. In another embodiment, the detecting includes visually observing the presence or absence of fluorescence.

In some embodiments, exposing the coated surface to radiation occurs after a predetermined period of time. In one embodiment, the substrate includes grout, cement clay, stone, brick, ceramic, polymer composite, wood, or a combination thereof. In another embodiment, the substrate includes marble, granite, limestone, wood, vinyl, linoleum, or a combination thereof. In other embodiments, the substrate includes a floor, a wall, or a pool. In another embodiment, the substrate is located in a structure selected from the group consisting of dwelling, garage, hospital, store, restaurant, school, office, and gymnasium. In other embodiments, the substrate includes an article selected from the group consisting of cooking articles, counter tops and laboratory bench tops. In some embodiments, the substrate includes furniture, fabric, woven web, nonwoven web, film or a combination thereof.

In one embodiment, the method further includes determining the fluorescence intensity. In other embodiments, the method further includes correlating the intensity of the fluorescence with the degree of wear on the coated surface.

In another embodiment, the composition includes wax, acrylate, urethane, epoxy, silicone, or a combination thereof. In other embodiments, the coating composition includes a floor finishing composition, antimicrobial compositions, mildew growth preventing compositions, or a polishing composition.

In some embodiments, the method further includes coating a second composition on the coated surface prior to exposing the coated surface to wear. In another embodiment, the method further includes coating a first layer and a second layer on the coated substrate after coating the substrate with the composition that includes a fluorescent compound. In other embodiments, the step of coating includes coating a portion of the substrate surface with the composition that includes a fluorescent compound. In one embodiment, the method further includes coating a first portion of the substrate surface with the composition that includes a fluorescent compound and coating a second portion of the substrate with a second composition, the second composition being essentially free of the fluorescent compound.

In other embodiments, exposing the coated surface to wear includes exposing the coated surface to pedestrian traffic. In another embodiment, exposing the coated surface to wear includes exposing the coated surface to repeated contact with other substrates.

In one embodiment, the method further includes exposing a first area of the coated surface to radiation capable of exciting the fluorescent compound, exposing a second area of the coated surface to radiation capable of exciting the fluorescent compound, the second area having experienced relatively more wear than the first area; and comparing the intensity of the fluorescence of the first area with the intensity of the fluorescence of the second area. In other embodiments, the method further includes i) exposing the coated surface to radiation capable of exciting the fluorescent compound prior to exposing the coated surface to wear, ii) detecting the intensity of the fluorescence emitted by the fluorescent compound at step (i), iii) exposing the coated substrate to radiation capable of exciting the fluorescent compound after exposing the coated surface to wear, iv) detecting the intensity of the fluorescence emitted by the fluorescent compound at step (iii), comparing the fluorescence intensity at step (ii) with the fluorescence intensity at step (iv).

In another aspect, the invention features a method of detecting wear on a substrate surface previously coated with a composition includes a fluorescent compound, the coated surface having been exposed to wear, the method includes exposing the surface to radiation capable of exciting the fluorescent compound, and detecting the presence or absence of fluorescence.

In other aspects, the invention features a method of determining the degree of wear on a coated surface of a substrate, the surface having previously been coated with a composition that includes a fluorescent compound, the method includes exposing the coated substrate to radiation capable of exciting a the fluorescent compound, measuring the fluorescence intensity emitted from the coated surface, and comparing the measured fluorescence intensity with a predetermined fluorescence intensity. In one embodiment, the predetermined fluorescence intensity includes a calibration curve. In other embodiments, the predetermined fluorescence intensity includes a fluorescence intensity value previously obtained from the coated substrate.

In some aspects, the invention features a method of detecting coverage of a coating on a substrate, the method includes, coating a substrate with a composition that includes a fluorescent dye essentially free of organosilicone, affixing the composition to the substrate, exposing the coated substrate to radiation capable of exciting the fluorescent dye, and detecting the presence or absence of fluorescence across the coated surface to determine the extent of surface coverage by the coating composition.

The invention features a method by which the presence or absence of a coating on a substrate surface can be easily and quickly determined through visual observation. A handheld ultraviolet light source such as a black light can be used to radiate the surface. The method is non-destructive and easy to perform.

The method includes employing a fluorescent indicator that, when properly selected, can be used without altering the look or aesthetics of the coating.

Other features and advantages will be apparent from the following description of the preferred embodiments and from the claims.

DETAILED DESCRIPTION

Figure 1:
FIG. 1 is a photograph of the coated surface of Example 1 radiated with black light.

The method of detecting wear on a coated substrate includes coating a substrate with a composition that includes a fluorescent compound, exposing the coated surface to wear, exposing the coated surface to radiation capable of exciting the fluorescent compound, and detecting (for example, observing) the presence or absence of fluorescence. The presence or absence of fluorescence provides information about the presence of wear on the coated surface and can also be used to determine the degree of wear on the coated surface. When the fluorescent compound is present it will fluoresce when excited by appropriate radiation, that is, radiation that can be absorbed by the fluorescent compound and that causes the fluorescent compound to emit in a visible spectrum.

The presence or absence of fluorescence is visible to the observer, which allows the observer to determine information about the surface including, for example, the extent of coating coverage on the coated surface, the degree of wear on the coated surface, the absence of coating on any portion of the coated surface, and combinations thereof. This information can then be used to determine how to treat the substrate surface including, for example, whether the surface should be refinished, whether additional composition should be applied, and whether another layer of coating should be applied to the surface. The absence of fluorescence, for example, indicates the absence of coating, which in turn can be used to indicate that the substrate requires a new coating. The presence of fluorescence indicates that the coating is present on the surface. A relatively low level of fluorescence may indicate that the coating has undergone a degree of wear but is still present on the surface.

The intensity of the fluorescence signal can be used to indicate the degree of wear on the surface and to provide further information as to when or whether the surface should be treated. A number of methods can be used to more accurately determine the degree of wear on the coated surface. In one method, an initial fluorescence intensity measurement is made after applying the coating on the substrate. The initial fluorescence intensity is then stored in a database including, for example, in an instrument, a computer, a notebook, the observer's memory, or a combination thereof. After a predetermined period of exposure to wear has elapsed, the fluorescence intensity is measured again. The second fluorescence intensity measurement is then compared to a predetermined intensity measurement including, for example, the initial fluorescence intensity measurement or a calibration curve. The calibration curve can be formulated such that it provides a correlation between an intensity value and a coating thickness. The fluorescence intensity comparison indicates the degree of wear on the surface, that is, the amount of coating that has worn away, and/or whether the surface should be treated.

In another method, the fluorescence intensity in a more highly trafficked area is compared to the fluorescence intensity of an area of relatively less traffic or essentially no traffic. This comparison can provide information as to the degree of wear on the more highly trafficked area, as well as whether the surface should be refinished.

The fluorescence intensity can be viewed by the observer or determined by an instrument capable of detecting fluorescence intensity. Examples of such instruments include fluorescence spectrometers, x-ray fluorescence spectroscopy, and emission spectroscopy.

The fluorescent compound present in the coating can be any fluorescent compound that will absorb in the ultraviolet spectrum and emit in the visible spectrum. Preferably the fluorescent compound absorbs radiation having a wavelength ranging of from 200 nm to 400 nm and emits light in the visible spectrum, that is, from 400 nm to 750 nm.

The fluorescent compound preferably does not absorb in the visible spectrum. Preferably the fluorescent compound is selected to be compatible with the composition into which it is being incorporated and does not impart visible color to the coating composition or alter the clarity of the coating composition. Suitable fluorescent compounds include, for example, fluorescent dyes, fluorescent pigments and combinations thereof. Examples of useful fluorescent dyes include sodium fluorescein, biphenyl fluorine, fluorine derivatives, rhodamine, pyrene, dansylamide, coumarin, carbopyronin, oxagin, naphthacene, distyryl diphyl derivatives, and combinations and derivatives thereof.

Suitable commercially available fluorescent dyes include, for example, Eccowhite (Eastern Color and Chemical Co., Greenville, S.C.), Flurol 7 GA, Calcofluor Yellow, Morton Yellow Green, Azosol Brilliant Yellow 6 GF, Rhodanine B, Rhodanine 6 GDN, Calcofluor White R, Blancophor White AW, Auramine and Eosine G.

Useful sources of radiation include any source that emits ultra violet light including, for example, hand held black light devices. Preferably the source of radiation emits radiation of a wavelength ranging from 400 nm to 750 nm.

The coating composition can be any composition suitable for treating a surface and capable of remaining on the surface for more than a transitory period. Examples of useful compositions include surface treatment compositions including, for example, waxes, finishes (for example, floor finishing compositions), sealants, polishing compositions, antimicrobial compositions, mildew growth preventing compositions, water repellent compositions, water proofing compositions, antigraffiti compositions, antisoiling compositions, and antislipping (that is, slip resistant) compositions. Useful floor finishing compositions include, for example, polymers including, for example, acrylates, polyesters and styrene, waxes, urethanes, epoxy and combinations thereof.

One example of a useful aqueous composition includes fluorescent compound, silane (for example, n-alkylalkoxysilane, condensates n-alkylalkoxysilane or a combination thereof), cationic quaternary ammonium surfactant and water. The composition preferably also includes siloxane (for example, methyl hydrogen siloxane methylhydrogen-methylalkyl siloxane copolymers (for example, methylhydrogen-dimethyl siloxane copolymers), methylhydrogen-cyclosiloxane copolymers and methylhydrogen-methylalkyl cyclosiloxane copolymers) and volatile carrier, that is, a carrier capable of volatilizing at room temperature after application on a substrate. Such compositions are disclosed in U.S. patent application Ser. No. 10/001,079, entitled, "Stain Resistant Treatment For Porous Substrates" filed Oct. 30, 2001, and incorporated herein.

A variety of application techniques are useful for coating the substrate surface including, for example, mopping, wiping, brushing, spraying, squeegeeing, soaking and combinations thereof.

The composition can be coated on the substrate in various constructions. The coating can be continuous or discontinuous. In one construction, the composition is coated on the entire surface of the substrate. Alternatively, the composition can be coated on a portion of the substrate surface, for example, in an area of the substrate that experiences the greatest amount of wear, for example, a high traffic area. The composition can also be provided as a layer disposed a distance from the exterior surface of the coated substrate. The coated surface can include, for example, multiple layers, where the fluorescent compound-containing layer is disposed beneath one or more layers. If at least one of the layers on top of the fluorescent layer block the excitation radiation from reaching the fluorescent compound, then when fluorescence is detected, the presence of fluorescence will indicate that the top layer(s) is no longer present and the fluorescent layer is exposed. Alternatively, where the layer (s) on top of the fluorescent compound-containing layer does not block the excitation radiation, the presence of fluorescence indicates that the fluorescence layer is present, and the absence of fluorescence indicates that the layer(s) above the fluorescent layer and the fluorescent layer are no longer present, for example, they have been worn away. The coating construction can also include multiple layers where at least two of the layers include a fluorescent compound and the fluorescent compound is the same or different from one layer to another.

Examples of suitable substrates include grout, cement, stone (for example, limestone, marble, and granite), clay, brick, ceramic, polymer composite, wood, vinyl, linoleum and combinations thereof. Useful substrates also include structures such as floors, walls (for example, sheet rock, shower walls, and kitchen walls), counter tops, table tops, laboratory bench tops, pools, cooking articles (for example, pots, pans, baking dishes and articles, and utensils), furniture, fabric, woven webs, nonwoven webs, film and combinations thereof. Other useful substrates are present in structures including, for example, dwellings (for example, homes, apartments, kitchens, bathrooms, laundry rooms), garages, hospitals, stores, restaurants, schools, gymnasiums, offices and stages.

The invention will now be described by way of the following examples. All ratios and percentages are by weight unless otherwise indicated.

EXAMPLES

Test Procedures

Test procedures used in the examples include the following.

Example 1

A fluorescent indicator mildew prevention composition was prepared by combining 0.0005% ECCOWHITE fluorescent dye (Eastern Color and Chemical Co., Greenville, S.C.) and SCOTCHGARD Mildew Shield mildew preventer solution (Minnesota Mining and Manufacturing Company, St. Paul, Minn.). The composition was applied on plasterboard, wood, grout and ceramic. The treated surfaces were exposed to mercury black light. The coating and defects therein were visible under the black light. The plasterboard results, radiated with black light, are depicted in the photograph in FIG. 1.

Example 2

Figure 2:
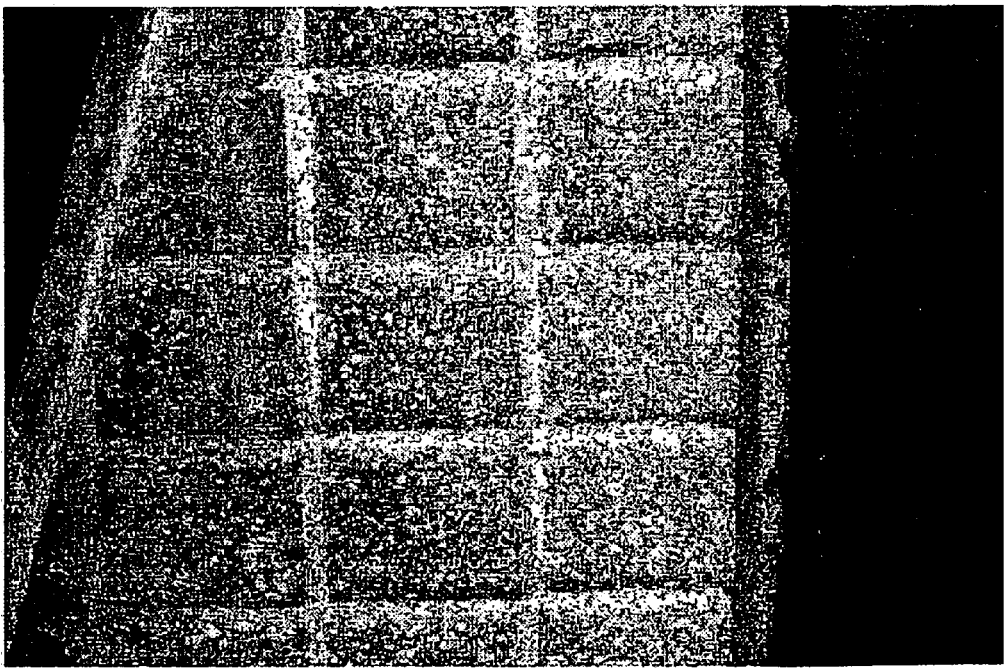
FIG. 2 is a photograph of the coated surface of Example 2 radiated with black light.

A grout and tile protector composition including fluorescent indicator was prepared by adding 0.0002% ECCOWHITE fluorescent dye to SCOTCHGARD grout protector aqueous solution (Minnesota Mining and Manufacturing Company). The composition was applied on ceramic tiles and grout. The treated surfaces were exposed to mercury black light. The coating and defects therein were visible under the black light. The results, radiated with black light, are depicted in the photograph in FIG. 2.

Example 3

Figure 3:
FIG. 3 is a photograph of the coated surface of Example 3 radiated with black light.

A floor finish coating was prepared by adding 0.0002% ECCOWHITE fluorescent dye to SPANGLE floor finishing composition (Minnesota Mining and Manufacturing Company). Three layers of the floor finishing composition were coated on the floor. Two floor tiles in a high traffic area were coated with two inches of the fluorescent dye-containing floor finishing composition. The treated floor was allowed to dry completely and two more layers were applied on top of the first layer. The first layer, that is, marker layer, was clearly seen when radiated with black light. The results, radiated with black light, are depicted in the photograph in FIG. 3.

Example 4

Figure 4:
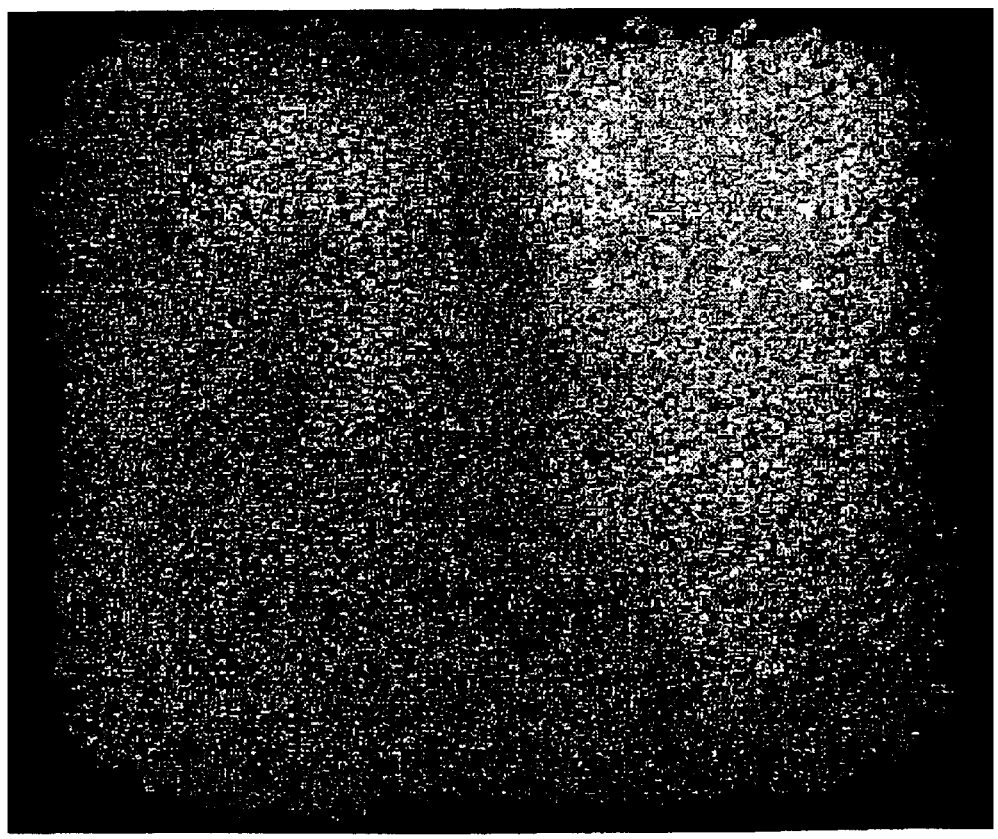
FIG. 4 is a photograph of the coated surface of Example 4 radiated with black light.

A carpet protector solution was prepared by adding 0.0001% ECCOWHITE fluorescent dye to SCOTCHGARD carpet protector solution (Minnesota Mining and Manufacturing Company). The composition was sprayed on carpeting and allowed to air dry. The degree of coating coverage on the carpet was then observed by radiating the coated carpet with black light. The results, radiated with black light, are depicted in the photograph in FIG. 4.

Other embodiments are within the claims.

What is claimed is:

1. A method of detecting wear on a substrate, said method comprising:
    a. coating a composition comprising a fluorescent compound on the surface of a substrate, wherein said composition is selected from waxes, floor finishing compositions, sealants, polishing compositions, antimicrobial compositions, water proofing compositions, antigraffiti compositions, antisoiling compositions, mildew growth preventing compositions, water repellent compositions, antislipping compositions, and polymer compositions;

b. exposing the coated surface to wear;

c. exposing the coated surface to ultraviolet radiation capable of exciting the fluorescent compound; and d. detecting the presence or absence of fluorescence.

2. The method of claim 1, wherein said radiation has a wavelength of from 200 nm to 400 nm.

3. The method of claim 1, wherein said fluorescent compound emits visible light.

4. The method of claim 1, wherein said fluorescent compound emits radiation having a wavelength of from 400 nm to 750 nm.

5. The method of claim 1, wherein said detecting comprises visually observing the presence or absence of fluorescence.

6. The method of claim 1, wherein exposing the coated surface to radiation occurs after a predetermined period of time.

7. The method of claim 1, wherein the substrate comprises grout, cement clay, stone, brick, ceramic, polymer composite, wood, or a combination thereof.

8. The method of claim 1, wherein the substrate comprises marble, granite, limestone, wood, vinyl, linoleum, or a combination thereof.

9. The method of claim 1, wherein the substrate comprises a floor, a wall, or a pool.

10. The method of claim 1, wherein the substrate is located in a structure selected from the group consisting of dwelling, garage, hospital, store, restaurant, school, office, and gymnasium.

11. The method of claim 1, wherein the substrate comprises an article selected from the group consisting of cooking articles, counter tops and laboratory bench tops.

12. The method of claim 1, wherein the substrate comprises furniture, fabric, woven web, nonwoven web, film or a combination thereof.

13. The method of claim 1, further comprising determining the fluorescence intensity.

14. The method of claim 13, further comprising correlating the intensity of the fluorescence with the degree of wear on the coated surface.

15. The method of claim 1, wherein said composition comprises wax, acrylate, urethane, epoxy or a combination thereof.

16. The method of claim 1, wherein said coating composition comprises a floor finishing composition, antimicrobial compositions, mildew growth preventing compositions, or a polishing composition.

17. The method of claim 1, further comprising coating a second composition on the coated surface prior to exposing said coated surface to wear.

18. The method of claim 1, further comprising coating a first layer and a second layer on said coated substrate after coating said substrate with said composition comprising a fluorescent compound.

19. The method of claim 1, wherein said step of coating comprises coating a portion of said substrate surface with said composition comprising a fluorescent compound.

20. The method of claim 1, further comprising coating a first portion of said substrate surface with said composition comprising a fluorescent compound and coating a second portion of said substrate with a second composition, said second composition being essentially free of said fluorescent compound.

21. The method of claim 1, wherein said exposing said coated surface to wear comprises exposing said coated surface to pedestrian traffic.

22. The method of claim 1, wherein said exposing said coated surface to wear comprises exposing said coated surface to repeated contact with other substrates.

23. The method of claim 1, further comprising
 i. exposing a first area of the coated surface to radiation capable of exciting the fluorescent compound;
 ii. exposing a second area of the coated surface to radiation capable of exciting the fluorescent compound, said second area having experienced relatively more wear than said first area; and
 iii. comparing the intensity of the fluorescence of said first area with the intensity of the fluorescence of said second area.

24. The method of claim 1, further comprising
 i. exposing the coated surface to radiation capable of exciting the fluorescent compound prior to exposing said coated surface to wear;
 ii. detecting the intensity of the fluorescence emitted by said fluorescent compound at step (i);
 iii. exposing the coated substrate to radiation capable of exciting the fluorescent compound after exposing said coated surface to wear;
 iv. detecting the intensity of the fluorescence emitted by said fluorescent compound at step (iii);
 v. comparing the fluorescence intensity at step (ii) with the fluorescence intensity at step (iv).

25. The method of claim 1, wherein said composition is selected from waxes, acrylates, urethanes, styrenes, polyesters, epoxy, silicone, or a combination thereof.

26. A method of detecting wear on a substrate surface, said method comprising:

a. providing a substrate that has been previously coated with a composition comprising a fluorescent compound, the coated surface having been exposed to wear, wherein said coating composition is selected from waxes, floor finishing compositions, sealants, polishing compositions; antimicrobial compositions, water proofing compositions, antigraffiti compositions, antisoiling compositions, mildew growth preventing compositions, water repellent compositions, antislipping compositions, and polymer compositions;

b. exposing the surface to ultraviolet radiation capable of exciting the fluorescent compound; and c. detecting the presence or absence of fluorescence.

27. The method of claim 26, further correlating the intensity of the fluorescence with the degree of wear on the coated surface.

28. A method of determining the degree of wear on a coated surface of a substrate, said method comprising:

a. providing a substrate surface having previously been coated with a composition comprising a fluorescent compound, wherein said coating composition is selected from waxes, floor finishing compositions, sealants, polishing compositions, antimicrobial compositions, water proofing compositions, antigraffiti compositions, antisoiling compositions, mildew growth preventing compositions, water repellent compositions, antislipping compositions, and polymer compositions;

b. exposing the coated substrate to ultraviolet radiation capable of exciting the fluorescent compound;

c. measuring the fluorescence intensity emitted from said coated surface; and d. comparing the measured fluorescence intensity with a predetermined fluorescence intensity.

29. The method of claim 28, wherein said predetermined fluorescence intensity comprises a calibration curve.

30. The method of claim 28, wherein said predetermined fluorescence intensity comprises a fluorescence intensity value previously obtained from the coated substrate.

31. The method of claim 28, further comprising correlating the intensity of the fluorescence with the degree of wear on the coated surface.

32. A method of detecting coverage of a coating on a substrate, said method comprising:

a. coating a substrate with a composition comprising a fluorescent dye, wherein said coating composition is selected from waxes, floor finishing compositions, sealants, polishing compositions, antimicrobial compositions, water proofing compositions, antigraffiti compositions, antisoiling compositions, mildew growth preventing compositions, water repellent compositions, antislipping compositions, and polymer compositions;

b. affixing said composition to said substrate;

c. exposing the coated substrate to ultraviolet radiation capable of exciting the fluorescent dye; and d. detecting the presence or absence of fluorescence across the coated surface to determine the extent of surface coverage by the coating composition.

33. The method of claim 32, Wherein said fluorescent dye is essentially free of organosilicone.

* * * * *

UNITED STATES PATENT AND TRADEMARK OFFICE
CERTIFICATE OF CORRECTION

PATENT NO. : 6,864,489 B2
DATED : March 8, 2005
INVENTOR(S) : Chen, Yen-Lane

It is certified that error appears in the above-identified patent and that said Letters Patent is hereby corrected as shown below:

Column 5,
Line 21, after "2001," insert -- Attorney Docket No. 57133US002 --.

Column 8,
Line 41, after "compositions" delete ";" and insert -- , --, therefore.

Column 10,
Line 13, delete "Wherein" and insert -- wherein --, therefore.

Signed and Sealed this

Fourteenth Day of June, 2005

JON W. DUDAS
*Director of the United States Patent and Trademark Office*